United States Patent [19]

Udvardy Nagy née Cserey Pechány et al.

[11] 4,390,625
[45] * Jun. 28, 1983

[54] METHOD FOR CONTROLLING THE AMOUNT AND DISTRIBUTION OF ALKALOIDS FORMED IN A FERMENTATION PROCESS

[75] Inventors: Eva Udvardy Nagy née Cserey Pechany; Miklós Budai; Gyorgy Fekéte; Sándor Görög; Bulcsu Herenyi; Géza Wack; Károly Zalai, all of Budapest, Hungary

[73] Assignee: Richter Gedeon Vegyeszeti Gyar RT, Budapest, Hungary

[ * ] Notice: The portion of the term of this patent subsequent to Jan. 18, 2000, has been disclaimed.

[21] Appl. No.: 232,173

[22] Filed: Feb. 6, 1981

[51] Int. Cl.$^3$ ...................... C12P 17/18; C12R 1/645
[52] U.S. Cl. ..................................... 435/119; 435/911
[58] Field of Search ................................ 435/119, 911

[56] References Cited

U.S. PATENT DOCUMENTS 2,835,675  5/1958  Abe et al. ............................ 435/119
3,110,651  11/1963  Kybal et al. ......................... 435/119
3,884,762  5/1975  Wock et al. ......................... 435/119

FOREIGN PATENT DOCUMENTS 1584464  2/1981  United Kingdom .

OTHER PUBLICATIONS

Czechoslovakian Inventor's Certificate CS202613 with accompanying English translation.

*Primary Examiner*—Alvin E. Tanenholtz
*Attorney, Agent, or Firm*—Karl F. Ross; Herbert Dubno

[57] ABSTRACT

The invention relates to a new method for controlling the level and distribution of alkaloids produced by *Claviceps purpurea* variant strains capable of producing primarily ergocornine, α-ergocryptine and β-ergocryptine under saprophytic conditions. According to the invention a compound of the biosynthesis path of isoleucine or a compound which promotes the formation of isoleucine by biochemical control is added to the fermentation broth. In other respects fermentation is performed under conditions known per se.

By the method of the invention the ratio of α- and β-ergocryptine formed in the fermentation broth can be adjusted to the optimum value.

3 Claims, No Drawings

METHOD FOR CONTROLLING THE AMOUNT AND DISTRIBUTION OF ALKALOIDS FORMED IN A FERMENTATION PROCESS

The invention relates to a new method of controlling the level and distribution of alkaloids produced by *Claviceps purpurea* variant strains capable of producing primarily ergocornine, α-ergocryptine and β-ergocryptine under saprophytic conditions.

It is known that dihydroergotoxine methanesulfonate or ethanesulfonate has an important role in therapy as a central metabolism controlling and central and peripheral circulation controlling agent. The substance promotes the protein synthesis of the central nervous system and inhibits catecholamine-stimulated adenylcyclase. Moreover, it has moderate sedative effects, it inhibits reflex tachycardia, improves cerebral circulation and lowers blood pressure. The substance is used in therapy primarily for the treatment of diseases connected with cerebral or peripheral circulation disorders.

Dihydroergotoxine is prepared by the hydrogenation of ergotoxine. The hydrogenated product is a mixture of dihydroergocrystine, dihydroergocornine and dihydroergocryptine (Hungarian patent specification No. 129,061). Dihydroergocryptine, one of the three components, may exist in two modifications [α and β forms, see Experientia 23, 991 (1967)], with slightly different pharmacological effects according to the most recent investigations. The α form is more active in conception-inhibiting tests performed on rats, whereas the β form exerts spinal effects, i.e. stronger vasopressor activity on decerebrated cats [Experientia 33, 1552 (1977)]. Therefore, dihydroergotoxine-containing compositions always have prescribed ratios of α- and β-dihydroergocryptine. The composition of dihydroergotoxine considered as ideal corresponds to a dihydroergocrystine:dihydroergocornine:α-dihydroergocryptine:β-dihydroergocryptine ratio of 3:3:2:1, and thus a 2:1 ratio of the α and β forms of dihydroergocryptine is regarded as optimum. The officially permitted deviation from this ideal ratio of 2:1 varies from country to country. According to the U.S. Pharmacopoeia and some European prescriptions the ratio of β-ergocryptine may vary between 26.7 and 44% calculated for the total ergocryptine content, whereas according to the regulations of some other European countries and Japan the permitted range is 28.6 to 40%.

The first step of the production of dihydroergotoxine methanesulfonate or ethanesulfonate is the preparation of the non-hydrogenated ergot alkaloid components, i.e. ergocrystine, ergocornine, β-ergocryptine and α-ergocryptine.

The components of the mixture are prepared by biological methods.

Biosynthesis may be performed parasitically on rye, whereupon the alkaloids produced are separated by plant extraction. This method is applied primarily for the preparation of ergocrystine. Strains utilized for this purpose are e.g. the strain deposited at the American Type Culture Collection under No. ATCC 20103 by the firm Società Farmaceutici Italia (see British patent specification No. 1,192,912) and the strain deposited at the Hungarian National Collection under No. MNG 00163 by the firm Gedeon Richter Pharmaceutical Co. Ltd.

Biosynthesis may also be performed in a saprophytic way, whereupon the alkaloids produced are separated from fermentation broths. The major methods and strains used for this purpose are as follows: the method of the British patent specification No. 1,158,380 utilizing an ergocryptine- and ergotamine-producing strain deposited under No. ATCC 20102; the method of the British patent specification No. 1,184,039 utilizing an ergocornine- and ergosine-producing strain deposited under No. ATCC 20106; the method of the U.S. Pat. No. 3,485,722 utilizing an ergocryptine-producing strain deposited under No. ATCC 20019; the method of the Belgian patent specification No. 824,987 utilizing a β-ergocryptine- and ergosine-producing strain deposited in the home collection of Società Farmaceutici Italia under No. FI 7374.

It appears from the above that these known strains produce not only the alkaloids used in the production or ergotoxine, but ergot alkaloids other than those of the ergotoxine type as well. Thus, with these strains, fermentation is not selective to ergotoxine.

Hungarian research workers were the first in selecting Claviceps purpurea strains which produce primarily ergocornine, α-ergocryptine and β-ergocryptine (the strain deposited under No. MNG 0022, see Hungarian patent specification No. 152,238, and the strain deposited under No. MNG 0088, see Hungarian patent specification No. 164,816). It has remained, however, an unsolved problem to control the ratio of the alkaloids produced by these strains during the fermentation process. The ratio of the three alkaloids produced could be adjusted to the required value only after fermentation by separating the individual components of the alkaloid mixture and mixing them again in the proper ratio. However, the individual ergot alkaloid components are difficult to separate from each other.

The Swiss patent specification No. 577,556 describes a process based on the simultaneous utilization of two strains. According to this method a strain which produces ergocornine, ergocryptine and isomers thereof is cultivated on a culture medium together with an ergocrystine-producing strain, and the alkaloids are produced simultaneously in a non-specified ratio. Thus, the alkaloid ratio cannot be adjusted by this method, either. Further problems arise from the fact that when two strains are applied simultaneously, fermentation is much more difficult to control than with the cultivation of a single strain.

H. Kobel (lecture held on the 1977 session of the Federation of the European Microbiological Societies) recognized that the biosynthesis of peptide alkaloids can be influenced by certain amino acids. More particularly, he presented the view that the biosynthesis of ergocornine, which contains valine in the peptide moiety, can be promoted by adding valine to the mixture, whereas the biosynthesis of α-ergocryptine, which contains leucine in the peptide chain, can be promoted by introducing leucine. In contrast, the biosynthesis of β-ergocryptine, which contains isoleucine in the peptide moiety, cannot be influenced favorably by introducing isoleucine. As a probable explanation of this strange phenomenon it was presumed that isoleucine inhibits the growth of fungus strains capable of producing β-ergocryptine.

Since, generally, the fermentation broths of the known strains which produce ergocryptine or ergocornine and ergocryptine contain just β-ergocryptine in a ratio less than required, the problem of adjusting the proper ratio has still remained unsolved. Therefore, we attempted to find a way of influencing the fermentation of *Claviceps purpurea* variant strains in a favorable direction.

It has been found unexpectedly that when, instead of isoleucine, a compound of the biosynthesis path of isoleucine (referred to hereinafter as a bioprecursor of isoleucine) is used to influence the alkaloid production of known *Claviceps purpurea* variant strains, the ratio of β-ergocryptine increases in the fermentation broth. Consequently, the bioprecursors of isoleucine do not inhibit the growth of the fungus strains.

It has also been found that the alkaloid production can also be controlled appropriately by compounds which promote the formation of isoleucine via biochemical control (i.e., biocontrolling compounds). Both the bioprecursors and the biocontrolling compounds are ketoacids, hydroxyacids and amino acids of 4 to 6 carbon atoms, the biosynthesis of which starts from aspartic acid or aspartic acid phosphate.

We have also attempted to influence the fermentation in the required direction by the use of a new variant strain obtained by selective cultivation. In these tests we succeeded in isolating a new variant of *Claviceps purpurea* with a yeast-like morphology, deposited at the Hungarian National Collection on 9th May, 1979 under No. MNG 00186. This strain produces primarily ergocornine and β-ergocryptine, thus it can be applied to increase the ratio of β-ergocryptine in fermentation broths.

Furthermore, it has been found that if the new variant strain is used for alkaloid production, and a bioprecursor of isoleucine or a biocontrolling compound which promotes the formation of isoleucine is added to the fermentation broth, the total alkaloid level of the broth increases, without influencing significantly the ratio of the individual alkaloids produced.

Based on the above, the invention relates to a new method for controlling the level and distribution of alkaloids produced by *Claviceps purpurea* variant strains capable of producing primarily ergocornine, α-ergocryptine and β-ergocryptine under saprophytic conditions. According to the invention a compound of the biosynthesis path of isoleucine or a compound which promotes the formation of isoleucine by biochemical control is added as controlling substance in the fermentation process otherwise performed under conditions known per se.

In the process of the invention a *Claviceps purpurea* strain which produces primarily ergocornine, α-ergocryptine an β-ergocryptine, preferably a variant strain deposited under No. MNG 0022, MNG 0088 or MNG 00186, is applied as alkaloid-producing strain.

Fermentation is performed in a submerged culture under aerobic conditions, utilizing a liquid culture broth which contains carbon and nitrogen sources, mineral salts and optionally other additives as well.

The strain is fermented at 20° to 26° C. for 4 to 8 days; the pH of the culture medium is maintained between 5.2 and 6.8.

Fermentation is performed in the presence of an additive which controls the ratio of the alkaloids produced. As additive controlling the ratio of the alkaloids a bioprecursor of isoleucine [Lehninger: Biochemistry; Worth Publ. Inc. N.Y. (1975), p. 704] or a biocontrolling agent which promotes the formation of isoleucine is used.

The bioprecursors of isoleucine and the sequence of their formation is as follows: α-ketobutyric acid [formed through homoserine and threonine or 3-methylaspartic acid (alternately 2-amino-3-methylsuccinic acid) and methyloxalic acid (alternately 2-methyl-3-oxosuccinic acid)], which converts in turn to α-acetyl-α-hydroxybutyric acid, α,β-dihydroxy-β-methylvaleric acid and α-keto-β-methylvaleric acid.

From biochemical aspects, the biocontrolling agents which promote the formation of isoleucine belong to the so-called aspartate family, i.e. their biosynthesis starts from aspartic acid or aspartic acid phosphate. These compounds are primarily ketoacids, hydroxyacids or amino acids of 4 to 6 carbon atoms, of which homocysteine and/or methionine are the most preferred.

The compound which regulates alkaloid production is applied in an amount of 0.01 to 10 kg/$m^3$ of fermentation broth, preferably 0.05 to 5.0 kg/$m^3$ of fermentation broth. The regulating additive is applied as an aqueous or slightly acidic aqueous solution, which is introduced into the fermentation broth after sterilization. The solution may be added either at once or in portions; alternately the solution can be introduced continuously during a certain period of fermentation.

The total alkaloid content of the fermentation broth was determined by photometry on the basis of color reactions. We do not consider this value as a specific characteristic of the process, although previous patent specifications frequently characterize the production levels in terms of the total alkaloid content determined by spectrophotometry.

To characterize the fermentation process, the individual ergotoxine components were determined separately by elution chromatography or quantitative liquid chromatography.

The invention is elucidated in detail by the aid of the following non-limiting Examples.

EXAMPLE 1

A culture of *Claviceps purpurea* MNG 0022 variant strain grown on AIC agar culture medium is inoculated onto 200 ml of a GK culture medium filled into a conical flask of 750 ml capacity, and is incubated for 3 days at 24° C. on a rotary shaker (300 r.p.m.). The resulting broth is applied to inoculate 5 liters of an St culture medium filled into a laboratory fermenter of 10 l capacity, and the mixture is fermented for 7 days to 24° C. under stirring at 240 r.p.m. and aerating at a rate of 0.5 liters of air/liter of fermentation broth/min. In the 40th, 64th, 88th and 112th hours of fermentation a 10% aqueous solution of methyl-oxalacetic acid is added to the broth as bioprecursor in an amount of 0.5 g of precursor/1 liter of fermentation broth. The ergocornine:ergocryptine ratio reaches the optimum level in the fermentation broth on the 7th day. At this stage fermentation is stopped. The total alkaloid level, determined by colour reaction, is 1150 γ/ml. According to thin layer chromatography [J. Chrom. 87, 433 (1973)] the fermentation broth contains 300 γ/ml of ergocornine and 180 γ/ml of ergocryptine, and the dextrorotatory epimers thereof amount to 110 γ/ml. Based on high pressure liquid chromatography [J. Pharm. Sci. 67, 98 (1978)], the ratio of α- and β-ergocryptine is 66:34.

The alkaloids are separated from the fermentation broth in a manner known per se.

The compositions of the culture media utilized in this Example are as follows:

| AIC agar medium: | |
| --- | --- |
| mannitol | 40.0 g |
| citric acid | 7.0 g |
| corn steep liquor | 2.0 g |
| potassium dihydrogen phosphate | 1.0 g |
| magnesium sulfate | 0.3 g |
| agar powder (Difco) | 25.0 g |
| ammonium hydroxide to pH 5.2–5.3 | |
| water | to 1000 ml |

The pH of the culture medium is adjusted to the required value (5.2–5.3) during boiling. Thereafter the culture medium is filled into test tubes in portions of 6 ml each, sterilized, and slant cultures are prepared.

| GK culture medium: | |
| --- | --- |
| trypcasine | 7.0 g |
| citric acid | 4.1 g |
| potassium dihydrogen phosphate | 0.3 g |
| magnesium sulfate | 0.3 g |
| ammonium hydroxide to pH 5.7–5.8 | |
| water | to 840 ml |

84 ml or 168 ml portions of the above mixtures are filled into flasks, and 16 ml or 32 ml, respectively, of a 50% glucose solution are added under sterile conditions.

| St culture medium: | |
| --- | --- |
| sucrose | 100.0 g |
| succinic acid | 10.0 g |
| potassium dihydrogen phosphate | 0.25 g |
| magnesium sulfate | 0.25 g |
| ammonium nitrate | 1.0 g |
| calcium chloride | 1.0 g |
| ammonium hydroxide to pH 5.2–5.3 | |
| water | to 1000 ml |

The culture medium is sterilized in portions of 0.1, 5 or 100 liters.

EXAMPLE 2

A culture of *Claviceps purpurea* MNG 0088 variant strain grown on AIC agar culture medium in inoculated onto 200 ml of a GK culture medium filled into a conical flask of 750 ml capacity, and is incubated for 3 days at 24° C. on a rotary shaker (300 r.p.m.). The resulting broth is applied to inoculate 5 liters of a TC 54 culture medium filled into a laboratory fermenter of 10 l capacity, and the mixture is fermented for 3 days at 24° C. under stirring at 240 r.p.m. and aerating at a rate of 0.5 liters of air/liter of fermentation broth/min. The resulting broth is applied to inoculate 100 liters of an St culture medium filled into an acid-fast fermenter equipped with a stirrer, and the mixture is fermented for 6 days at 24° C. under stirring at 120 r.p.m. and aerating at a rate of 0.3 liters of air/liter of fermentation broth/min. In the first 5 days of fermentation a 5% aqueous solution of α-ketobutyric acid is added to the broth as precursor at a rate of 20 ml/hour.

The total alkaloid level of the broth obtained after stopping fermentation is 920 γ/ml. The concentrations of the individual alkaloids were determined by the chromatographic methods described in Example 1. According to this measurement the broth contains 260 γ/ml of ergocornine, 155 γ/ml of α-ergocryptine and 95 γ/ml of β-ergocryptine, furthermore 80 γ/ml of ergocorninine-cryptinine.

The compositions of the AIC, GK and St culture media are the same as given in Example 1.

The TC-54 culture medium has the following composition:

| | |
| --- | --- |
| sucrose | 100.0 g |
| citric acid | 10.0 g |
| sodium chloride | 10.0 g |
| potassium dihydrogen phosphate | 0.5 g |
| magnesium sulfate | 0.5 g |
| ammonium hydroxide to pH 5.7–5.8 | |
| water | to 1000 ml |

The culture medium is sterilized in a laboratory fermenter in portions of 5 liters.

EXAMPLE 3

A culture of *Claviceps purpurea* MNG 0088 variant strain grown on St agar culture medium is inoculated onto 100 ml of a GK culture medium filled into a conic flask of 500 ml capacity, and is incubated for 3 days at 24° C. on a rotary shaker (300 r.p.m.). 10 ml of the resulting culture are applied to inoculate 100 ml of a T 25 culture medium, and the mixture is incubated for 5 days at 20° C. under shaking as described above. In the 20th hour of fermentation 0.5 g of threonine are added to the broth as precursor. On the 5th day of fermentation the total alkaloid level of the broth amounts to 1200 γ/ml. The concentrations of ergocornine and ergocryptine were determined as described in Example 1. According to this measurement the broth contains 260 γ/ml of ergocornine, 140 γ/ml of α-ergocryptine and 80 γ/ml of β-ergocryptine. The total amount of ergocorninine and -cryptinine is 130 γ/ml.

The composition of the GK culture medium is the same as described in Example 1.

St agar culture medium:

25 g of powdered agar (Difco) are added to each liter of the St culture medium with the composition given in Example 1, the resulting mixture is boiled, then distributed to flasks in portions of 6 ml each, sterilized, and slant cultures are prepared.

| T 25 culture medium: | |
| --- | --- |
| sucrose | 300.0 g |
| citric acid | 15.0 g |
| yeast extract | 1.0 g |
| potassium dihydrogen phosphate | 0.5 g |
| magnesium sulfate | 0.5 g |
| ammonium hydroxide to pH 5.2–5.3 | |
| water | to 1000 ml |

The culture medium is distributed to flasks in portions of 100 ml and sterilized.

EXAMPLE 4

One proceeds as described in Example 3 with the difference that 0.5 g of homoserine are added to the broth as precursor instead of threonine. On the 5th day of fermentation the total alkaloid level of the broth amounts to 880 γ/ml. The broth contains 220 γ/ml of ergocornine, 150 γ/ml of α-ergocryptine and 80 γ/ml of β-ergocryptine. The total amount of ergocorninine and -cryptinine is 180 γ/ml

EXAMPLE 5

One proceeds as described in Example 3 with the difference that 0.05 g of homocysteine are added to the broth as precursor, instead of threonine. On the 5th day of fermentation the total alkaloid level of the broth amounts to 700 γ/ml. The broth contains 190 γ/ml of ergocornine, 85 γ/ml of α-ergocryptine and 90 γ/ml of β-ergocryptine. The total amount of ergocorninine and ergocryptinine is 150 γ/ml.

EXAMPLE 6

A culture of *Claviceps purpurea* MNG 00186 variant strain grown on St agar culture medium is inoculated onto 100 ml of a GK culture medium filled into a conical flask of 500 ml capacity, and is incubated for 4 days at 24° C. on a rotary shaker (300 r.p.m.). 10 ml portions each of the resulting culture are applied to inoculate 8 flasks containing 100 ml of St culture medium, each. The cultures are fermented for 7 days at 24° C. under shaking as described above. A solution of 0.02 g of methionine in 2 ml of water is added to 4 of the 8 flasks in the 24th and 48th hours of fermentation, whereas the remaining 4 flasks, to which no precursor is added, serve as controls. Fermentation is stopped on the 7th day, the control broths (i.e. the contents of the flasks without precursor) are combined, and the alkaloid content of the broth is determined. The broth contains 80 γ/ml of ergocornine, 15 γ/ml of α-ergocryptine and 30 γ/ml of β-ergocryptine.

The contents of the flasks to which precursor was added are combined as well, and the alkaloid content of the broth is determined. The broth contains 250 γ/ml of ergocornine, 50 γ/ml of α-ergocryptine and 100 γ/ml of β-ergocryptine.

The compositions of culture media GK, St and St-agar are the same as given in Examples 1 and 3, respectively.

What we claim is:

1. A fermentation process for the preparation of ergot alkaloids which comprises:

cultivating a *Claviceps purpurea* variant strain capable of producing primarily ergocornine, alpha-ergocryptine and beta-ergocryptine, while submerged in a liquid aerated culture broth containing carbon and nitrogen sources, at a temperature of 20°–26° for 4 to 8 days at a pH between 5.4 and 6.8;

employing *Claviceps purpurea* MNG 00186 as the *Claviceps purpurea* variant strain capable of producing primarily ergocornine, alpha-ergocryptine and beta-ergocryptine; and adding to said culture broth a sufficient amount of a compound selected from the group consisting of a $C_4$ to $C_6$ keto acid, a $C_4$ to $C_6$ hydroxy acid, or a $C_4$ to $C_6$ amino acid, wherein said compound is (a) a bioprecursor of isoleucine, or (b) a compound having the ability to promote the formation of isoleucine, to obtain a higher yield of said ergot alkaloids as well as to increase the percentage of the beta-ergocryptine in said ergot alkaloids.

2. A fermentation process for the preparation of ergot alkaloids which comprises:

cultivating a *Claviceps purpurea* variant strain capable of producing primarily ergocornine, alpha-ergocryptine, and beta ergocryptine, while submerged in a liquid aerated culture broth containing carbon and nitrogen sources, at a temperature of 20°–26° C. for 4 to 8 days at a pH between 5.4 and 6.8; and adding to said culture broth a sufficient amount of a compound having the ability to promote the formation of isoleucine selected from the groups consisting of homocysteine and methionine, to obtain a higher yield of said ergot alkaloids as well as to increase the percentage of the beta-ergocryptine in said ergot alkaloids.

3. A fermentation process for the preparation of ergot alkaloids which comprises:

cultivating a *Claviceps purpurea* variant strain capable of producing primarily ergocornine, alpha-ergocryptine and beta-ergocryptine, while submerged in a liquid aerated culture broth containing carbon and nitrogen sources, at a temperature of 20°–26° C. for 4 to 8 days at a pH between 5.4 and 6.8;

employing *Claviceps purpurea* MNG 00186 as the *Claviceps purpurea* strain capable of producing primarily ergocornine, alpha-ergocryptine and beta-ergocryptine; and adding to said culture broth a sufficient amount of a compound having the ability to promote the formation of isoleucine selected from the group consisting of homocysteine and methionine, to obtain a higher yield of said ergot alkaloids as well as to increase the percentage of the beta-ergocryptine in said ergotalkaloids.

* * * * *